United States Patent [19]

Manne

[11] Patent Number: 5,564,127
[45] Date of Patent: Oct. 15, 1996

[54] PUNCTURE PROOF SURGICAL GLOVE

[76] Inventor: Joseph Manne, 115 E. 9th St., #3P, New York, N.Y. 10003

[21] Appl. No.: 429,619

[22] Filed: Apr. 27, 1995

[51] Int. Cl.$^6$ .................................................. A41D 13/10
[52] U.S. Cl. ................... 2/161.7; 2/167; 2/169
[58] Field of Search ........................... 2/161.7, 168, 167, 2/169, 2.5, 161.6, 159, 16

[56] References Cited

U.S. PATENT DOCUMENTS

| | | | |
|---|---|---|---|
| D. 202,329 | 9/1965 | Swistel | D3/11 |
| 1,146,638 | 7/1915 | Miller. | |
| 2,373,940 | 4/1942 | Beall | 2/168 |
| 2,864,091 | 12/1958 | Schneider. | |
| 4,004,295 | 1/1977 | Byrnes, Sr. | 2/167 |
| 4,218,779 | 8/1980 | Hart | 2/168 |
| 4,283,244 | 8/1981 | Hashmi | 2/164 |
| 4,493,865 | 1/1985 | Kuhlmann | 2/16 |
| 4,526,828 | 7/1985 | Fogt | 2/7 |
| 4,694,508 | 9/1987 | Iriyama. | |
| 4,742,578 | 5/1988 | Seid | 2/168 |
| 4,779,290 | 10/1988 | Welch | 2/167 |
| 4,825,470 | 5/1989 | Horio | 2/21 |
| 4,833,733 | 5/1989 | Welch | 2/169 |
| 4,858,245 | 8/1989 | Sullivan | 2/21 |
| 4,864,661 | 9/1989 | Gimbel | 2/167 |
| 4,881,277 | 11/1989 | Hogle | 2/169 |
| 4,888,829 | 12/1989 | Kleinerman | 2/167 |
| 4,924,530 | 5/1990 | Tagaya | 2/163 |
| 5,014,361 | 5/1991 | Gray | 2/167 |
| 5,014,362 | 5/1991 | Tillotson et al.. | |
| 5,020,162 | 6/1991 | Kersten | 2/164 |
| 5,031,245 | 7/1991 | Milner | 2/168 |
| 5,036,551 | 8/1991 | Dailey | 2/168 |
| 5,039,750 | 8/1991 | Miller | 2/168 |
| 5,045,341 | 9/1991 | Shlenker | 2/167 |
| 5,069,965 | 12/1991 | Esemplare. | |
| 5,070,540 | 12/1991 | Bettcher. | |
| 5,070,543 | 12/1991 | Beck | 2/163 |
| 5,088,124 | 2/1992 | Dutchik. | |
| 5,088,125 | 2/1992 | Ansell. | |
| 5,089,205 | 2/1992 | Huang. | |
| 5,113,532 | 5/1992 | Sutton. | |
| 5,123,119 | 6/1992 | Dube. | |
| 5,130,159 | 7/1992 | Shlenker. | |
| 5,133,087 | 7/1992 | Machida. | |
| 5,133,090 | 7/1992 | Modak. | |
| 5,138,719 | 8/1992 | Orlianges. | |
| 5,173,966 | 12/1992 | DeLeo. | |
| 5,180,605 | 1/1993 | Milner. | |
| 5,187,815 | 2/1993 | Stern. | |
| 5,196,263 | 3/1993 | Melby. | |
| 5,259,069 | 11/1993 | Gimbel. | |

OTHER PUBLICATIONS

Miscellaneous advertisements for surgical gloves.

*Primary Examiner*—Amy B. Vanatta
*Attorney, Agent, or Firm*—Lucas & Just

[57] ABSTRACT

The puncture proof surgical glove employs a rolled, warp knitted material to prevent punctures. The rolled, warp knitted material is made from solid filaments having a diameter of 0.03 to 0.004 inches, a tensile strength greater than 690,000 kPa and a modulus of elasticity less than or equal to about 205,000 MPa. The rolled, warp knitted material is made from the filaments which are helical in shape and interlocking such that the helical filament has an inside diameter of 0.008 inches, an outside diameter of 0.018 inches, a pitch of 0.034 inches, and a thickness of 0.037 inches. The warp knitted material is rolled such that it is flattened to a thickness of 0.025 inches.

7 Claims, 1 Drawing Sheet

PUNCTURE PROOF SURGICAL GLOVE

BACKGROUND OF THE INVENTION

This invention relates to gloves and, more specifically, to a puncture-proof glove for use in surgery.

An intact barrier between the hand of a surgeon and the tissue of a patient undergoing an operation is important if transmission of a disease in either direction is to be prevented. Conventionally, surgical gloves are used to provide such a barrier. The surgical glove was introduced in 1889 and it has now become common practice for surgeons as well as all medical technicians to wear surgical gloves in order to prevent infections in either direction.

Currently, a majority of surgical gloves are made from latex. In recent years the effectiveness of surgical gloves in preventing transmission of a disease has been questioned. It is not uncommon for a surgical glove to become punctured without the wearer's knowledge, thereby allowing for the transmission of disease in either direction. Such undetected punctures may result in prolonged contact with an infected material. In order to prevent these undetected punctures, it has become common practice for medical personnel to wear two pairs of gloves, referred to as "double gloving". Double gloving has been found to provide some protection in that if the outer glove becomes punctured, the inner glove continues to provide protection. The inner glove, however, is not puncture-proof and there remains a need for a puncture-proof glove for use by medical personnel.

Prior solutions to making a puncture-proof glove included the use of meshes of various kinds of materials, leather gloves, multi-layered gloves, gloves with patches of antiseptic solution, and fingertip protection of solid materials. Some of these prior art solutions restrict the flexibility of the surgeon's hand. Needless to say, medical personnel need a high degree of flexibility, especially when they are wearing gloves for surgery.

SUMMARY OF THE INVENTION

The surgical glove of the present invention has been found to be both highly puncture resistant, puncture-proof, and extremely flexible, thereby not restricting the flexibility of the surgeon's hand. The surgical glove of the present invention employs a rolled, warp knitted material to provide both needlestick protection (puncture-proof) and flexibility. Specifically, it has been found that a flexible, puncture resistant glove can be made by using a rolled, warp knitted material made from a filament that has a tensile strength greater than about 690,000 kPa (kilopascal, 100,000 psi) and a modulus of elasticity less than or equal to about 205,000 MPa ($3 \times 10^7$ psi). The rolled, warp knitted material has very small openings which are resistant to puncture by even 25 gauge needles. The rolled, warp knitted material, however, also allows for greater flexibility for, unlike normal interwoven mesh, the design of the rolled, warp material allows for extensive rotation around the long axis while it also allows for longitudinal sliding which is necessary for flexion along the axis parallel to the axis of the filaments that make up the material.

Preferably, the rolled, warp knitted material is used in conjunction with a conventional latex surgical glove to prevent both punctures and fluid contact. More specifically, the improved surgical glove of the present invention comprises: (a) a first glove member made of a flexible material which completely covers the hand and a portion of the wrist, said first glove member having four finger stalls and a thumb stall, said flexible material being a thin elastomeric material which is impervious to fluid, bacteria and viruses, said glove member having a ventral side and a dorsal side; and (b) a rolled, warp knitted material affixed to the ventral side of said first glove member, said rolled, warp knitted material being made from interlocking helical filaments, each of said filaments having a diameter of about 0.03 to 0.004 inches, said filament having a tensile strength greater than about 690,000 kPa and a modulus of elasticity less than or equal to about 205,000 MPa, said rolled, warp knitted material being made by means of a process comprising the steps of first forming a sheet of warp knitted material from a plurality of continuous helical filaments which are positioned side-by-side and are interlocking, each of said helical filaments being screwed into an adjacent helical filament such that each helical filament interlocks with the adjacent helical filament, each of said helical filaments having an inside diameter of about 0.008 inches and an outside diameter of about 0.018 inches, said sheet of warp knitted material having a thickness of about 0.037 inches and a helical pitch of about 0.034 inches in said sheet of material; and, subsequently, flattening said sheet of warp knitted material by means of a roller to reduce the thickness of said sheet of material to about 0.025 inches and to produce said rolled, warp knitted material.

As a minimum, the rolled, warp knitted material must cover the ventral side of the finger and thumb stalls. More preferred is that, the rolled, warp knitted material covers not only the ventral side of the thumb and finger stalls but also the ventral side of the palm of said glove member. Even more preferred, the rolled, warp knitted material covers not only the ventral side of the palm, thumb and fingers, but also extends up the sides to a level about half way to the dorsal side of the glove. More preferably, the rolled, warp knitted material totally encompasses the glove to include the wrist portion. Where the rolled, warp knitted material has edges that might puncture the glove members, the edges of the rolled, warp knitted material should be treated to prevent such puncturing. Additionally, in order to provide maximum flexibility, where the rolled, warp knitted material extends up the side of the hand and fingers, slits should be made at each finger joint that run perpendicular to the plane of the palm. These slits aid in providing flexibility to the glove of the present invention.

The rolled, warp knitted material can be affixed to said first glove member in a number of ways. It may be adhered to either the outside or the inside of the glove using a suitable adhesive material. The interstices of the rolled, warp knitted material should not be filled with the adhesive. When the adhesive fills the interstices of the rolled, warp knitted material, the flexibility of the glove decreases. Alternatively, a second glove member which is substantially identical to the first glove member can be used such that the rolled, warp knitted material is interposed between said first glove member and said second glove member. By interposing the rolled, warp knitted material between the two glove members, the rolled, warp knitted material is affixed to the first glove member. When interposing the rolled, warp knitted material between the two glove members, adhesives can be used to help fix the position of the rolled, warp knitted material between the two gloves.

The first glove member and the second glove member are made from conventional surgical glove material such as natural rubber, polyvinyl, polyurethane, natural rubber latex, polyacrylates, polybutadiene, styrene-butadiene copolymer, acrylonitrile butadiene rubber and neoprene (polychloroprene). Such materials can also be used as adhesives to adhere the rolled, warp knitted material to the first glove member.

The filaments used to make the rolled, warp knitted material are any material that can be formed into a solid filament having a diameter of about 0.03 to 0.004 inches wherein the filament has a tensile strength greater than about 690,000 kPa and a modulus of elasticity less than or equal to about 205,000 MPa, and can be formed into a rolled, warp knitted material as herein described. The tensile strength and modulus of elasticity are measured in a conventional way using conventional equipment. Suitable materials include glass fibers, aramid, nylon, and metal wire. Metal wire is preferred. Suitable metal wire includes brass, nickel, stainless steel, steel, tungsten, titanium and alloys thereof. The preferred metal wire is stainless steel and, more specifically, type 304 stainless steel. The diameter of the filament used to make the rolled, warp knitted material is about 0.03 to 0.004 inches; and preferably about 0.01 to 0.005 inches. Good results have been obtained with a filament having a diameter of about 0.006 inches. The metal wire used to manufacture the rolled, warp knitted material is not coated with any type of material. The metal wire is woven in its natural uncoated state, thereby allowing for easy sterilization of the rolled, warp knitted material prior to it becoming affixed to the first glove member. With respect to the non-metallic materials, they must be specially processed to impart to the rolled, warp knitted material the equivalent puncture resistance as is provided to the rolled, warp knitted material by the metal filaments. Suitable techniques include thermopultrusion.

A critical aspect of the present invention is how the rolled, warp knitted material is made. It is the process for making the rolled, warp knitted material which provides the flexibility necessary for the invention while preventing punctures.

The rolled, warp knitted material used in the present invention is made in the following sequential steps:

First, a warp knitted material is made from individual filaments which are wound into a helix using a preformed filament rather than a filament which has been extruded simultaneously with the formation of the helix. Preferably, the helix is formed such that it has an outside diameter of about 0.018 inches and an inside diameter of about 0.008 inches. The number of helices per linear inch is preferably about 76 helices per linear inch. The helical pitch diameter is preferably about 0.034 inches.

After formation of the individual helices, the helices are made interlocking by winding one helix into another to form a sheet of material where one helix is next to the other and the adjacent helices are interlocking. Since all the helices run in the warp direction of the material and there are no helices or filaments that run in the woof direction of the material, the material is referred to as a warp knitted material.

After formation of the warp knitted material, the material is subject to a roller action which reduces the thickness of the material and alters a number of its other physical attributes. Specifically, the roller flattens the helices. Preferably, the action of the roller reduces the thickness of the material to about 0.025 inches. Also, after rolling, the number of helices per linear inch is reduced to preferably about 59. In order to insure that the material has the proper flexibility, a roller must be used rather than a press. The roller maintains the uniformity of the material. Such rolled, warp knitted material is conventional, and can be obtained from Standard Chain of North Attleboro, Mass.

These and other aspects of the present invention may be more fully understood by reference to one or more of the following drawings.

DETAILED DESCRIPTION OF THE DRAWINGS

Figure 1:
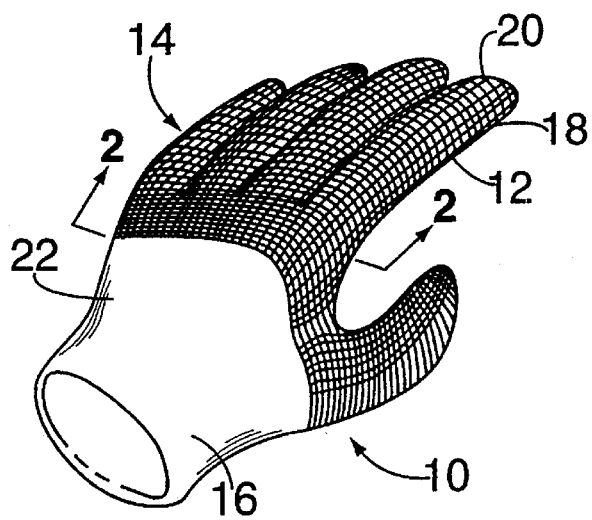
FIG. 1 is a perspective view of a surgical glove constructed in accordance with the present invention.
Figure 2:
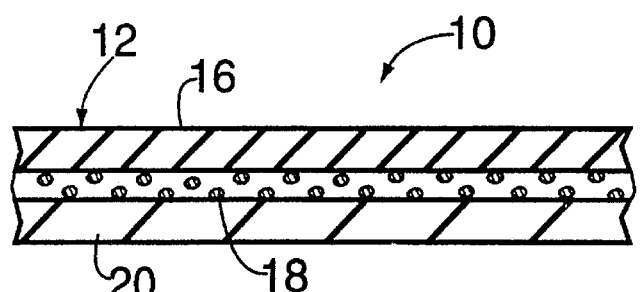
FIG. 2 is a fragmental cross section taken along lines 2—2 of FIG. 1 showing the ventral side.

A surgical glove constructed in accordance with the present invention having the rolled, warp knitted material on both the ventral and dorsal sides is shown in FIG. 1. Note that the slits at each finger joint are not depicted. The glove 10 includes a ventral side generally indicated at 12 and a dorsal side generally indicated at 14. The sides 12 and 14 include a first glove member 16 of a stretchable air and water impermeable material. Over first glove 16 is laid the rolled, warp knitted material 18. Glove 10 also includes a second stretchable air and water impermeable second glove member 20 (FIG. 2) which is positioned over the rolled, warp knitted material 18. Rolled, warp knitted material 18 is puncture resistant. As shown in FIG. 2, rolled, warp knitted material 18 is shown interposed between the first glove member 16 and the second glove member 20. Note that there is no material disposed in the interstices of the rolled, warp knitted material 18. This embodiment provides a puncture resistant surface not only on the ventral and dorsal sides, but also along the sides of the finger and thumb stalls.

Figure 3:
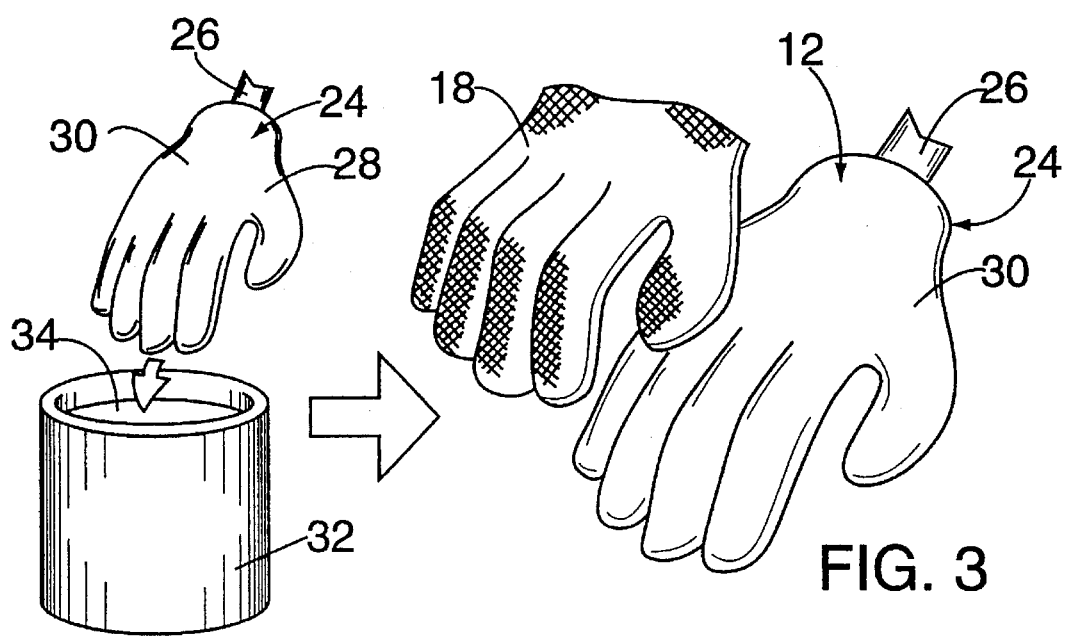
FIG. 3 is a schematic perspective view showing a method for making the glove of the present invention.

It is not essential in accordance with the present invention that the dorsal side 14 of the glove 10 be covered by the rolled, warp knitted material 18. As shown in FIG. 3, only the ventral side of the glove made in accordance with the present invention has rolled, warp knitted material 18.

A method for making the surgical glove 10 in accordance with the present invention is illustrated in FIG. 3. A mold shell 24 includes handle portion 26 and hand form portion 28. The hand form portion 28 includes a dorsal side (not shown in the figure) and a ventral side 30. The hand form portion 28 is dipped into container 32 of liquid 34. Liquid 34 is a curable material which is stretchable and air and water impervious, e.g. latex. This curable material forms said first glove member 16 after the hand form portion 28 is removed from liquid 34. A hand shaped layer of rolled, warp knitted material 18 is then placed onto the ventral side of the shell 24 prior to the complete curing of liquid 34 on shell 24 by placing rolled, warp knitted material 18 onto hand shell 24. Because the liquid 34 has not completely cured, it is still tacky and will cause rolled, warp knitted material 18 to become affixed to the ventral side of first glove member 16 without filling the interstices of the rolled knitted warp material.

In the preferred embodiment of the present invention, a second glove member is formed in the same manner as the first glove member. After the liquid 34 used to make the second glove member has completely cured on a moldshell similar to mold shell 24, the second glove member is removed from the mold shell and stretched over the outside of rolled, warp knitted material 18 and first glove member 16. In this manner, rolled, warp knitted material 18 has become interposed between both first glove member 16 and second glove member 20. Also, as evident from FIG. 2, liquid 34 does not fill the interstices of rolled, warp knitted material 18.

An alternative to making the surgical glove of the present invention with a second glove on top of first glove member and the rolled, warp knitted material interposed therebetween, is for a surgeon to wear a second conventional surgical glove on the outside of the surgical glove made in accordance with the present invention comprising only first glove member and rolled, warp knitted material. In this way a surgical glove in accordance with the present invention is made and has the second glove member associated therewith.

Alternatively, two conventional surgical gloves are employed and the rolled, warp knitted material is positioned therebetween. The friction between the surgical gloves and the rolled, warp knitted material is enough to maintain the position of the rolled, warp knitted material with respect to the hand.

It will be appreciated that the use of rolled, warp knitted material can be employed in other forms of protective clothing besides a surgical glove. For instance, it could be used for leggings, face protection, aprons, etc.

It will be understood that the claims are intended to cover all changes and modifications of the preferred embodiments of the invention herein chosen for the purpose of illustration which do not constitute a departure from the spirit and scope of the invention.

What is claimed is:

1. A surgical glove comprising:

(a) a first glove member made of a flexible material which completely covers the hand and a portion of the wrist, said first glove member having four finger stalls and a thumb stall, said flexible material being a thin elastomeric material which is impervious to fluid, bacteria and viruses, said glove member having a ventral side and a dorsal side; and (b) a rolled, warp knitted material affixed to the ventral side of said first glove member, said rolled, warp knitted material being made from interlocking helical filaments wherein said filaments have a diameter of about 0.03 to 0.004 inches, said filaments having a tensile strength greater than about 690,000 kPa and a modulus of elasticity less than or equal to about 205,000 MPa, said rolled, warp knitted material being made by means of a process comprising a first step of forming a sheet of warp knitted material from a plurality of continuous helical filaments which are positioned side-by-side and are interlocking, each of said helical filaments being screwed into an adjacent helical filament such that each helical filament interlocks with the adjacent helical filament, each of said helical filaments having an inside diameter of about 0.008 inches and an outside diameter of about 0.018 inches, said sheet of warp knitted material having a thickness of about 0.037 inches and a helical pitch of about 0.034 inches in said material; subsequently, flattening said sheet of warp knitted material by means of a roller to reduce the thickness of said material to about 0.025 inches and to produce said rolled, warp knitted material.

2. The surgical glove of claim 1 wherein said rolled, warp knitted material covers the ventral side of the finger and thumb stalls.

3. The surgical glove of claim 1 wherein said rolled, warp knitted material covers the ventral side of the thumb and finger stalls and the ventral side of the palm.

4. The surgical glove of claim 1 wherein said rolled, warp knitted material covers the ventral side of the palm, thumb stall and finger stall and extends up the sides of the glove to a level of about half way to the dorsal side of the glove.

5. The surgical glove of claim 1 wherein said rolled, warp knitted material totally encompasses said first glove member.

6. The surgical glove of claims 1, 2, 3, 4 or 5 further comprising a second glove member, said second glove member being affixed to the outside of said first glove member and said rolled, warp knitted material.

7. The surgical glove of claims 1, 2, 3, 4 or 5 wherein said first glove member is made from a material selected from the group consisting of natural rubber, polyvinyl, polyurethane, natural rubber, latex, polyacrylates, polybutadiene, styrene-butadiene copolymer, acrylonitrile butadiene rubber and neoprene.

* * * * *